(12) United States Patent
Hirata et al.

(10) Patent No.: US 8,669,284 B2
(45) Date of Patent: Mar. 11, 2014

(54) PHARMACEUTICAL COMPOSITION COMPRISING A BI-CYCLIC COMPOUND AND METHOD FOR STABILIZING THE BI-CYCLIC COMPOUND

(75) Inventors: Ryu Hirata, Sanda (JP); Yasuhiro Harada, Sanda (JP); Ryuji Ueno, Potomac, MD (US)

(73) Assignees: Sucampo AG, Zug (CH); R-Tech Ueno, Ltd., Tokyo (JP)

( * ) Notice: Subject to any disclaimer, the term of this patent is extended or adjusted under 35 U.S.C. 154(b) by 192 days.

(21) Appl. No.: 13/161,060

(22) Filed: Jun. 15, 2011

(65) Prior Publication Data

US 2011/0244036 A1 Oct. 6, 2011

Related U.S. Application Data

(63) Continuation of application No. 11/656,513, filed on Jan. 23, 2007, now Pat. No. 7,985,770.

(60) Provisional application No. 60/761,362, filed on Jan. 24, 2006.

(51) Int. Cl.
*A61K 9/64* (2006.01)
*A61K 31/352* (2006.01)

(52) U.S. Cl.
USPC .......................................... 514/456; 424/456

(58) Field of Classification Search
USPC ......................................................... 514/456
See application file for complete search history.

(56) References Cited

U.S. PATENT DOCUMENTS

| | | | |
|---|---|---|---|
| 4,358,603 A | 11/1982 | Yu | |
| 4,780,316 A | 10/1988 | Brox | |
| 5,073,569 A | 12/1991 | Ueno et al. | |
| 5,166,174 A | 11/1992 | Ueno et al. | |
| 5,212,324 A | 5/1993 | Ueno | |
| 5,221,763 A | 6/1993 | Ueno et al. | |
| 5,443,842 A | 8/1995 | Seghizzi et al. | |
| 5,739,161 A | 4/1998 | Ueno | |
| 6,242,485 B1 | 6/2001 | Ueno | |
| 6,414,016 B1 | 7/2002 | Ueno | |
| 6,583,174 B1 | 6/2003 | Ueno et al. | |
| 6,610,732 B2 | 8/2003 | Ueno | |
| 6,818,226 B2 | 11/2004 | Reed et al. | |
| 2007/0129340 A1 | 6/2007 | Katsuki et al. | |

FOREIGN PATENT DOCUMENTS

| | | |
|---|---|---|
| EP | 1 172 104 A1 | 1/2002 |
| JP | 3-218315 A | 9/1991 |
| JP | 5-70354 A | 3/1993 |
| JP | 10-287532 A | 10/1998 |
| JP | 2004-182614 A | 7/2004 |
| WO | 00/50029 A1 | 8/2000 |
| WO | 01/05388 A2 | 1/2001 |
| WO | 01/27099 A2 | 4/2001 |
| WO | 02/20007 A1 | 3/2002 |
| WO | 03/041716 A1 | 5/2003 |
| WO | 2005/002588 A1 | 1/2005 |
| WO | 2005/074943 A1 | 8/2005 |
| WO | 2006/025599 A1 | 3/2006 |

OTHER PUBLICATIONS

Japanese Office Action dated Aug. 7, 2012 for corresponding Application No. 2008-535214.
Heidi Van Orden, Constipation: An Overview of Treatment; Journal of Pediatric Health Care (2004): 18, 320-322.
Tao, Zhou and Yong, Ren. "Soft Gelatin Capsule", Guangzhou Pharmaceutical Packaging Materials Factory, Tonghe, Guangzhou, China, Jun. 30, 1996.
Extended European Search Report for Application No. 1318335.4 dated Dec. 5, 2013, 7 pages.
Reich G.; Wirkungsweise and Optimierung des Weichmacherzusatzes in Weichgelatinekapseln; Pharmazeutische Industrie 1994 DE, vol. 56, No. 10, 1994, pp. 915-920.

*Primary Examiner* — Walter Webb
(74) *Attorney, Agent, or Firm* — Sughrue Mion, PLLC

(57) ABSTRACT

Disclosed is a method for stabilizing a pharmaceutically active bi-cyclic compound of formula (I):

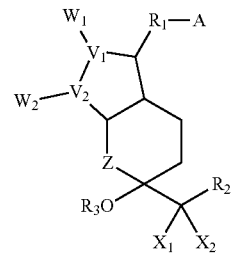

comprising the step of: admixing the same with a polyol and/or a fatty acid ester other than glyceride and a composition obtained by the method. In addition a soft gelatin capsule formulation of the compound of formula (I) obtained by incorporating the compound in a soft gelatin capsule shell comprising gelatin and a polyol plasticizer.

10 Claims, No Drawings

PHARMACEUTICAL COMPOSITION COMPRISING A BI-CYCLIC COMPOUND AND METHOD FOR STABILIZING THE BI-CYCLIC COMPOUND

CROSS REFERENCE TO RELATED APPLICATION

This is a continuation of application Ser. No. 11/656,513 filed Jan. 23, 2007, which claims the benefit of U.S. Provisional Application No. 60/761,362 filed Jan. 24, 2006, the disclosure of which is incorporated by reference.

FIELD OF THE INVENTION

The present invention relates to a method for stabilizing a therapeutically effective bi-cyclic compound and a soft gelatin capsule formulation of the bi-cyclic prostaglandin compound.

BACKGROUND ART

The instant inventors have revealed that a bi-cyclic compound such as

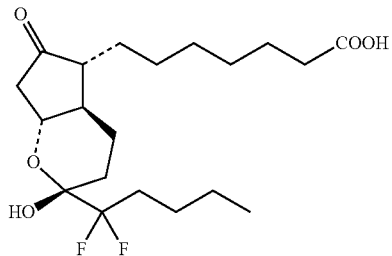

7-[(2R,4aR,5R,7aR)-2-(1,1-difluoropentyl)-2-hydroxy-6-oxooctahydrocyclopenta[b]pyran-5-yl]heptanoic acid is useful for treating or preventing constipation and the stability of the compound can be improved by admixing the same with a glyceride (see WO2001/027099 (U.S. Pat. No. 6,583,174) and WO2002/020007 (U.S. Pat. Nos. 6,414,016 and 6,610,732), the contents of these references are herein incorporated by reference.).

To date, there is no information about how a solvent other than glyceride affects on the stability of the bi-cyclic compound.

SUMMARY OF THE INVENTION

An object of the present invention is to provide a method for improving stability of a therapeutically active bi-cyclic prostaglandin compound. Another object of the invention is to provide an orally administrable dosage form of the bi-cyclic compound which has an excellent shelf stability.

Accordingly, the present invention provides a composition comprising a bi-cyclic compound represented by the formula (I):

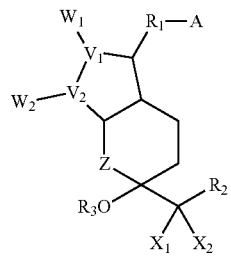

wherein, A is —CH$_2$OH, —COCH$_2$OH, —COOH or a functional derivative thereof;
X$_1$ and X$_2$ are hydrogen, lower alkyl or halogen;
V$_1$ and V$_2$ are carbon or oxygen;
W$_1$ and W$_2$ are

wherein R$_4$ and R$_5$ are hydrogen, hydroxy, halogen, lower alkyl, lower alkoxy or hydroxy (lower) alkyl with the proviso that R$_4$ and R$_5$ are not hydroxy or lower alkoxy at the same time;
Z is a carbon, oxygen, sulfur or nitrogen;
R$_1$ is a saturated or unsaturated bivalent lower-medium aliphatic hydrocarbon residue which is unsubstituted or substituted with halogen, lower alkyl, hydroxy, oxo, aryl or heterocyclic group;
R$_2$ is a saturated or unsaturated, lower or medium aliphatic hydrocarbon residue which is unsubstituted or substituted with halogen, oxo, hydroxy, lower alkyl, lower alkoxy, lower alkanoyloxy, lower cycloalkyl, lower cycloalkyloxy, aryl, aryloxy, heterocyclic group or heterocyclicoxy group; lower cycloalkyl; lower cycloalkyloxy; aryl, aryloxy, heterocyclic group or heterocyclicoxy group; and
R$_3$ is a hydrogen, lower alkyl, lower cycloalkyl, aryl or heterocyclic group;
and a polyol and/or fatty acid ester other than glyceride.

In another aspect of the invention, a method for stabilizing the above-specified bi-cyclic compound which comprises: dissolving said compound in a polyol and/or fatty acid ester other than glyceride.

Further, the present invention provides a soft gelatin capsule formulation of the above-specified bi-cyclic compound, which comprises:
a soft gelatin capsule shell comprising gelatin and a polyol as a plasticizer, and
a mixture comprising bi-cyclic compound of formula (I) and a pharmaceutically acceptable vehicle, which is filled in the shell.

Further more, the present invention provides a method for stabilizing the bi-cyclic compound of formula (I), which comprises:
dispersing or mixing the bi-cyclic compound in a pharmaceutically acceptable vehicle to give a liquid mixture, and incorporating the liquid mixture in a soft-gelatin capsule whose shell comprises gelatin and a polyol as a plasticizer.

DETAILED DESCRIPTION OF THE PREFERRED EMBODIMENTS

In the above formula (I), the term "unsaturated" in the definitions for R$_1$ and R$_2$ is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 2 to 8 carbon atoms for $R_1$ and 1 to 10, especially 1 to 8 carbon atoms for $R_2$.

The term "halogen" covers fluorine, chlorine, bromine and iodine. Particularly preferable is a fluorine.

The term "lower" is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, sec-butyl, t-butyl, pentyl and hexyl.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "lower cycloalkyl" refers to a cyclic group formed by cyclization of a lower alkyl group as defined above but contains three or more carbon atoms, and includes, for example, cyclopropyl, cyclobutyl, cyclopentyl and cyclohexyl.

The term "lower cycloalkyloxy" refers to the group of lower-cycloalkyl-O—, wherein lower cycloalkyl is as defined above.

The term "aryl" may include unsubstituted or substituted aromatic hydrocarbon rings (preferably monocyclic groups), for example, phenyl, naphthyl, tolyl, xylyl. Examples of the substituents are halogen atom and halo(lower)alkyl, wherein halogen and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen and lower alkyl group are as described above.

The term "heterocyclicoxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, sec-butyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower) alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, sec-butyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

Examples of the amides are mono- or di-lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred A is —COOH, —CH$_2$OH, or its pharmaceutically acceptable salt, ester, ether or amide.

Preferred combination of $X_1$ and $X_2$ is that at least one of $X_1$ and $X_2$ is halogen, and more preferably, both of them are halogen, especially fluorine.

Preferred $W_1$ is =O, or where one of $R_4$ and $R_5$ is hydrogen, another is hydroxyl.

Preferred $W_2$ is where $R_4$ and $R_5$ are both hydrogen.

Preferred Z is an oxygen.

Preferred $R_1$ is an unsubstituted saturated or unsaturated bivalent lower-medium aliphatic hydrocarbon residue. It may preferably have 1 to 10 carbon atoms, more preferably, 2 to 8 carbon atoms.

Examples of $R_1$ include, for example, the following groups:

—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—CH($CH_3$)—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred $R_2$ is a saturated or unsaturated bivalent lower-medium aliphatic hydrocarbon residue. It may preferably have 1 to 10 carbon atoms, more preferably, 1 to 8 carbon atoms.

Preferred $R_3$ is a hydrogen.

The bi-cyclic compounds according to the present invention encompass not only the compounds represented by the above formula (I) but also optic isomers, steric isomers, and tautomeric isomers thereof.

It has been known that a bi-cyclic compound having the formula as shown below (Tautomer II) may be in equilibrium with its tautomeric isomer, 13,14-dihydro-15-keto-prostaglandin compound (tautomer I) (U.S. Pat. Nos. 5,166,174, 5,225,439, 5,284,858, 5,380,709, 5,428,062 and 5,886,034, the contents of these cited references are herein incorporated by reference.)

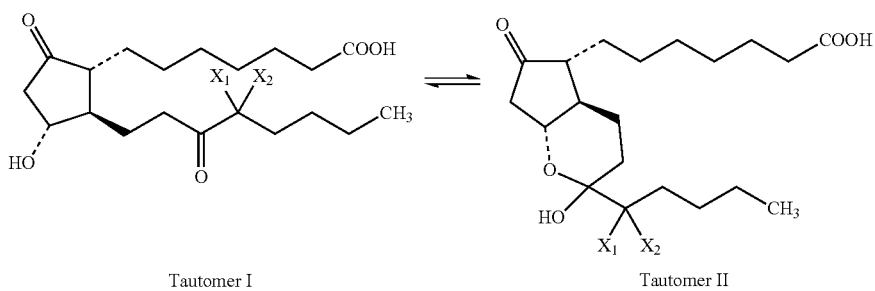

Tautomer I ⇌ Tautomer II

It is considered that the halogen atom(s) at $X_1$ and/or $X_2$ promote bi-cyclic ring formation, such as the compound 1 or 2 below. In addition, in the absence of water, the tautomeric compounds as above exist predominantly in the form of the bi-cyclic compound. In aqueous media, it is supposed that hydrogen bonding occurs between the water molecule and, for example, the keto group on the hydrocarbon chain, thereby hindering bi-cyclic ring formation. The bi-cyclic/mono-cyclic structures, for example, may be present in a ratio of 6:1 in $D_2O$; 10:1 in $CD_3OD$-$D_2O$ and 96:4 in $CDCl_3$. Accordingly, a preferable embodiment of the present invention is the composition in which the bi-cyclic form is present in ratio of bi-cyclic/mono-cyclic of at least 50:50, preferably 90:10, or even greater to substantially all bi-cyclic compound; 100% bi-cyclic compound is within this invention.

Preferred embodiment of the compound of the present invention includes the Compounds 1 and 2 shown below:

Compound 1:

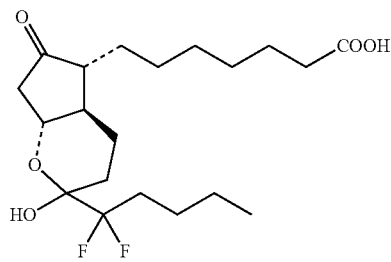

7-[(2R,4aR,5R,7aR)-2-(1,1-difluoropentyl)-2-hydroxy-6-oxooctahydrocyclopenta[b]pyran-5-yl]heptanoic acid Compound 2:

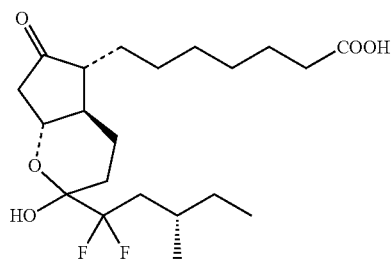

7-{(4aR,5R,7aR)-2-[(3S)-1,1-difluoro-3-methylpentyl]-2-hydroxy-6-oxooctahydrocyclopenta[b]pyran-5-yl}heptanoic acid The compounds of the present invention possess some pharmacological activities for example, are useful for treating constipation. See WO2001/027099 (U.S. Pat. No. 6,583,174) and WO2002/020007 (U.S. Pat. Nos. 6,414,016 and 6,610,732).

Some of the bi-cyclic compounds used in the present invention may be prepared by the method disclosed in WO2001/027099 (U.S. Pat. No. 6,583,174), WO2002/020007 (U.S. Pat. Nos. 6,414,016 and 6,610,732), U.S. Pat. Nos. 5,073,569, 5,166,174, 5,221,763, 5,212,324, 5,739,161 and 6,242,485, the contents of these references are herein incorporated by reference.

The pharmaceutical composition of the present invention comprises the bi-cyclic compound of formula (I) and a polyol and/or fatty acid ester other than glyceride.

The polyol used in the present invention is an alcohol having two or more hydroxy groups, and those having two or three hydroxy groups, such as glycerin, polyethylene glycol and propylene glycol, are preferably used.

The fatty acid ester other than glyceride used in the invention is an ester of fatty acid and an alcohol other than glycerin. Preferred fatty acid which consists the fatty acid ester is a medium or higher chain fatty acid having at least C6, preferably C6-24 carbon atoms, for example caproic acid (C6), caprylic acid (08), capric acid (C10), lauric acid (C12) and myristic acid (C14), palmitic acid (C16), palmitoleic acid (C16), stearic acid (C18), oleic acid (C18), linoleic acid (C18), linolenic acid (C18), ricinolic acid (C18) and arachic acid (C20). Preferred alcohols which consists the fatty acid ester may comprise C1-6 monovalent alcohols and polyols such as polyethylene glycol and propylene glycol.

Preferred fatty acid esters may include a propylene glycol ester of a saturated or unsaturated fatty acid which may have a branched chain. A fatty acid ester derived from a fatty acid and a monovalent alcohol is also preferably used in the instant invention. The fatty acid ester may preferably be an ester of C8-20 fatty acid and a C2-3 monovalent alcohol, such as isopropyl myristate, isopropyl palmitate, ethyl linoleate and ethyl oleate.

The pharmaceutical composition of the present invention may be obtained by dissolving or dispersing the above-described bi-cyclic compound in the above described polyol and/or fatty acid ester other than glyceride. When it is difficult to dissolve the bi-cyclic compound directly in the polyol and/or fatty acid ester other than glyceride, each of them may be dissolved in a solvent in which both of them are soluble respectively, and then the solutions may be combined. In this embodiment, the solvent may be removed under vacuum.

The amount of the polyol and/or fatty acid ester other than glyceride in the composition relative to the amount of the bi-cyclic compound is not limited as long as the bi-cyclic compound is stable in the composition. In general, the amount of the polyol and/or fatty acid ester other than glyceride per one part of the bi-cyclic compound may be 1-5,000,000, preferably, 5-1,000,000 and most preferably, 10-500,000 parts by weight.

In a preferred embodiment, the composition of the present invention is substantially free of water. The term "substantially free of water" means that the composition does not contain water that is intentionally added. It is understood that many materials contain water that is taken up from the atmosphere or is present as a coordination complex in its normal state. Water taken up by hygroscopic materials or present as a hydrate is permissibly present in the compositions of this embodiment. According to the embodiment, any water that is present in the composition should not be present in amounts such that the water will have a deleterious effect to the composition of the present invention.

The composition of the present invention may further comprise physiologically acceptable additives which do not provide adverse effect to the stability of the compound of the formula (I). The additives which may be employed in the present invention include, but not limited to, excipients, diluents, fillers, solvents, lubricants, adjuvants, binders, disintegrants, coatings, capsulating agents, ointment bases, suppository base, aerozoles, emulsifiers, dispersing agents, suspensions, viscosity increasing agents, isotonic agents, buffers, analgesic agents, preservatives, anti-oxidants, corrigents, flavors, colorants, and functional agents such as cyclodextrin, biologically degradable polymers. The details of the additives may be selected from those described in any of general textbooks in the pharmaceutical field. The composition of the present invention may further comprise one or more other pharmaceutically active ingredient.

The pharmaceutical composition of the present invention may be formulated by a conventional manner. They may be in the form suitable for oral administration, suppository, injection, or topical administration such as eye drops or ointments.

According to the present invention, a soft gelatin capsule formulation of a compound of formula (I) wherein the compound of formula (I) dissolved or mixed in a pharmaceutically acceptable vehicle is filled in soft gelatin capsule shell comprising gelatin and a polyol plasticizer is also provided.

According to this embodiment, the pharmaceutically acceptable vehicle is not specifically limited as long as the vehicle can dissolve or disperse the bi-cyclic compound of formula (I) therein and does not significantly deteriorate the stability of the compound. In view of manufacturing soft gelatin capsule formulation, a solvent which is liquid at the room temperature is preferable. A solution, dispersion or mixture of the bi-cyclic compound in the solvent may be filled in the capsule shell.

Examples of the pharmaceutically acceptable vehicles may include fatty acid esters, i.e. an ester of fatty acid and an alcohol, and polyols.

Preferred fatty acid which consists the fatty acid ester is a medium or higher chain fatty acid having at least C6, preferably C6-24 carbon atoms, for example caproic acid (C6), caprylic acid (C8), capric acid (C10), lauric acid (C12) and myristic acid (C14), palmitic acid (C16), palmitoleic acid (C16), stearic acid (C18), oleic acid (C18), linoleic acid (C18), linolenic acid (C18), ricinolic acid (C18) and arachic acid (C20). Preferred alcohols which consists the fatty acid ester may comprise C1-6 monovalent alcohol and polyols such as glycerin, polyethylene glycol and propylene glycol.

Preferred fatty acid esters may include a glyceride or a propylene glycol ester of a saturated or unsaturated fatty acid which may have a branched chain. Two or more glycerides may be used as a mixture.

Examples of the mixture of glycerides are mixture of caprylic acid triglyceride and capric acid triglyceride, vegetable oils such as castor oil, corn oil, olive oil, sesame oil, rape oil, salad oil, cottonseed oil, camellia oil, peanut oil, palm oil, and sunflower oil.

A fatty acid ester derived from a fatty acid and a monovalent alcohol is also preferably used as a pharmaceutically acceptable vehicle. The fatty acid ester may preferably be an ester of C8-20 fatty acid and a C2-3 monovalent alcohol, such as isopropyl myristate, isopropyl palmitate, ethyl linoleate and ethyl oleate.

Examples of polyols may preferably include alcohols having two or three hydroxy groups such as glycerin, polyethylene glycol and propylene glycol.

According to the present invention, the mixture which is filled in the soft-gelatin capsule shell may be obtained by dissolving or dispersing the above-described bi-cyclic compound in the above described pharmaceutically acceptable vehicle which is liquid at the room temperature. When it is difficult to dissolve the bi-cyclic compound directly in the vehicle, each of them may be dissolved in a solvent in which both of them are soluble respectively, and then the solutions may be combined.

The amount of the vehicle in the mixture relative to the amount of the bi-cyclic compound is not limited as long as the bi-cyclic compound is stable in the final formulation. In general, the amount of the vehicle per one part of the bi-cyclic compound may be 1-5,000,000, preferably, 5-1,000,000 and most preferably, 10-500,000 parts by weight.

The mixture of the invention may further comprise an oil solvent such as mineral oil, liquid paraffin, and tocopherol.

The mixture of the present invention may further comprise another pharmaceutically active ingredient.

According to the present invention, the shell of the soft gelatin capsule is manufactured from gelatin and a polyol as a plasticizer. The amount of the polyol used for preparing the shell of the soft gelatin capsule is not specifically limited as long as the physical properties of the resulting capsule is not deteriorated. In general, the amount of polyol plasticizer is 20-60 parts by weight, preferably, 30-50 parts by weight per 100 parts by weight of gelatin.

The soft gelatin capsule formulation of the bi-cyclic compound may be manufactured according to a conventional manner using the above described liquid mixture and a mixture of gelatin and the plasticizer.

The present invention will be explained in more detail by means of the following examples, which are illustrated by way of example only and never intended to limit the scope of the present invention.

Example 1

Compound 1 was dissolved in a vehicle shown in table 1 below to give 240 μg/g solution (sample). The precise concentration of Compound 1 in the solution was determined by means of HPLC (day 0). Then, the solution was put in a hard grass container and kept at 55° C. for 10 days, and then the precise concentration of the compound 1 in the solution was determined by means of HPLC (day 10).

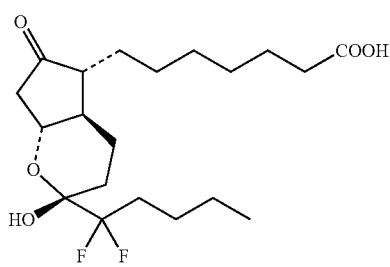 [SMILES: CCCCC(F)(F)[C@@]1(O)CC[C@H]2[C@@H](CC(=O)[C@@H]2CCCCCCC(=O)O)O1]

Compound 1

The determination of the concentration of the compound in the sample was carried out as follows. About 0.2 g of the sample was mixed with exactly 2 ml of internal standard solution and then with a dissolving agent shown in Table 1 to give 5 mL of sample solution. About 12 mg of the reference standard compound 1 was weighted precisely and added with acetonitrile to give exactly 100 ml solution. Exactly 0.8 ml of the solution was obtained and added with exactly 4 ml of the internal standard solution, and then added with the dissolving agent to give 10 ml of standard solution.

The fluorescent labeling agent was added to the respective solution, stirred and stood at room temperature. Then, the respective solution in an amount that theoretically gives 3.6 ng of compound 1 was loaded on the column and analyzed under the condition as follows:

HPLC Analysis Condition:
Column: 5 mm×25 cm stainless steel column packed with octadecylsilane treated silica gel for HPLC (5 μm)
Mobile phase: mixture of acetonitrile HPLC grade: methanol HPLC grade: ammonium acetate (0.05 mol/L)
Temperature: 35° C.
Detector: spectrophotofluorometer Results are shown in Table 1

TABLE 1

| Concentration of compound 1 after 55° C. storage | | | | |
|---|---|---|---|---|
| | vehicle | dissolving agent | day 0[1] | day 10[1] |
| 1 | glycerin | methanol | 92.0% | 78.0% |
| 2 | propylene glycol | acetonitrile | 97.8% | 88.6% |
| 3 | polyethylene glycol 400 | acetonitrile | 98.2% | 90.1% |
| 4 | propylene glycol ester of fatty acid | acetonitrile | 99.9% | 89.0% |
| 5 | isopropyl palmitate | acetonitrile | 98.9% | 99.1% |

[1]percentage based on the theoretical amount (240 μg/g)

Comparative Example 1

According to the same manner as described in Example 1, stability of the bi-cyclic compound in various vehicles was measured. The vehicles and results are shown in Table 2.

TABLE 2

| Concentration of compound 1 after 55° C. storage | | | | |
|---|---|---|---|---|
| | vehicle | dissolving agent | day 0[1] | day 10[1] |
| 1 | hydrogenated maltose starch syrup | acetonitrile/ water(1:1) | — | 24.4% |
| 2 | sugar alcohol solution derived from corn starch | methanol | — | 26.3% |
| 3 | oleic acid | methanol | 101.7% | 57.3% |
| 4 | linolenic acid | acetonitrile | 74.8% | 33.1% |

[1]percentage based on the theoretical amount (240 μg/g)
[2]Polysorb 85/70/00 ™, ROQUETTE AMERICA, Inc.

According to the results of Example 1 and Comparative Example 1, the stability of compound 1 is significantly improved by admixing the same with a polyol and/or a fatty acid ester other than glyceride.

Example 2

One hundred (100) parts by weight of gelatin (Type A, high bloom, SKW Biosystems #195F) and 35 parts by weight of glycerin, a plasticizer, were mixed in water and dried to give gelatin piece whose water content was about 4%. Compound 1 was dissolved in medium chain fatty acid triglyceride (USP/NF grade) to give a liquid mixture comprising 60 μg/g of the compound. 0.5 g of the liquid mixture and 0.5 g of gelatin piece were put together in a sealed container and kept at 40° C. for 21 days. The concentration of compound 1 contained in the liquid mixture was determined in the same manner as Example 1. As a result, the amount of the compound 1 at day 21 was 97.0% on the basis of a theoretical amount (60 μg/g).

According to the Example 2, the stability of the bi-cyclic compound of formula (I) can be improved by incorporating the same into gelatin capsule comprising a polyol as a plasticizer.

Example 3

Glycerin in an amount shown in Table 3 was added in an appropriate amount of water, stirred and heated. Then, gelatin 100 parts by weight was added thereto to give gelatin solution. Compound 1 was dissolved in medium chain fatty acid triglyceride (USP/NF grade) to give a fill solution containing 240 μg/g of compound 1. The gelatin solution and the fill solution were loaded on capsule forming and filling machine to give capsule containing the fill solution, and dried to give soft gelatin capsule.

The capsule was put in a sealed container and kept at 40° C. for 2 months. The concentration of compound 1 in the fill solution contained in the capsule was determined after 1 and 2 months storage in the same manner as EXAMPLE 1.

TABLE 3

Stability of soft gelatin capsule of compound 1

| soft gelatin capsule | | conc. (% of Initial) 40° C. | |
|---|---|---|---|
| (parts by weight) | | 1 mo | 2 mo |
| gelatin | 100 | glycerin | 45 | 100.0% | 98.7% |
| | | | 55 | 97.7% | 94.0% |

What is claimed is:

1. A soft gelatin capsule formulation of a bi-cyclic compound of formula (I):

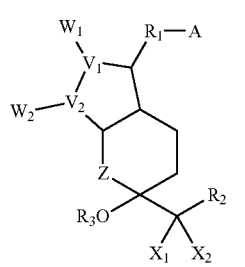

(I)

wherein, A is —CH$_2$OH, —COCH$_2$OH, —COOH or a functional derivative thereof;
X$_1$ and X$_2$ are hydrogen, lower alkyl or halogen;
V$_1$ and V$_2$ are carbon or oxygen;
W$_1$ and W$_2$ are

wherein R$_4$ and R$_5$ are hydrogen, hydroxy, halogen, lower alkyl, lower alkoxy or hydroxy (lower) alkyl with the proviso that R$_4$ and R$_5$ are not hydroxy or lower alkoxy at the same time;
Z is a carbon, oxygen, sulfur or nitrogen;
R$_1$ is a saturated or unsaturated bivalent lower-medium aliphatic hydrocarbon residue which is unsubstituted or substituted with halogen, lower alkyl, hydroxy, oxo, aryl or heterocyclic group;
R$_2$ is a saturated or unsaturated, lower or medium aliphatic hydrocarbon residue which is unsubstituted or substituted with halogen, oxo, hydroxy, lower alkyl, lower alkoxy, lower alkanoyloxy, lower cycloalkyl, lower cycloalkyloxy, aryl, aryloxy, heterocyclic group or heterocyclicoxy group; lower cycloalkyl; lower cycloalkyloxy; aryl, aryloxy, heterocyclic group or heterocyclicoxy group;
R$_3$ is hydrogen, a lower alkyl, lower cycloalkyl, aryl or heterocyclic group, which comprises:

a soft gelatin capsule shell comprising gelatin and a polyol selected from the group consisting of glycerin, propylene glycol and polyethylene glycol as a plasticizer, and
a mixture comprising said bi-cyclic compound and glyceride, which is filled in the shell.

2. The formulation of claim 1, wherein
A is —COOH or functional derivative thereof;
X$_1$ and X$_2$ are halogen;
W$_1$ is =O, or where one of R$_4$ and R$_5$ is hydrogen, another is hydroxy;
W$_2$ is where R$_4$ and R$_5$ are both hydrogen;
Z is oxygen;
R$_1$ is a saturated or unsaturated bivalent unsubstituted lower-medium aliphatic hydrocarbon residue;
R$_2$ is a saturated or unsaturated unsubstituted lower-medium aliphatic hydrocarbon residue;
R$_3$ is hydrogen.

3. The formulation of claim 1, wherein the polyol is glycerin.

4. The formulation of claim 1, wherein the glyceride is a medium chain fatty acid triglyceride.

5. A method for stabilizing a bi-cyclic compound of formula (I):

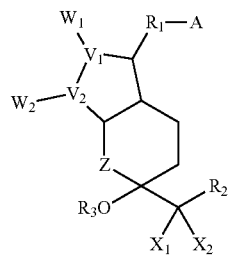

(I)

wherein, A is —CH$_2$OH, —COCH$_2$OH, —COOH or a functional derivative thereof;
X$_1$ and X$_2$ are hydrogen, lower alkyl or halogen;
V$_1$ and V$_2$ are carbon or oxygen;
W$_1$ and W$_2$ are

wherein R$_4$ and R$_5$ are hydrogen, hydroxy, halogen, lower alkyl, lower alkoxy or hydroxy (lower) alkyl with the proviso that R$_4$ and R$_5$ are not hydroxy or lower alkoxy at the same time;
Z is a carbon, oxygen, sulfur or nitrogen;
R$_1$ is a saturated or unsaturated bivalent lower-medium aliphatic hydrocarbon residue which is unsubstituted or substituted with halogen, lower alkyl, hydroxy, oxo, aryl or heterocyclic group;
R$_2$ is a saturated or unsaturated, lower or medium aliphatic hydrocarbon residue which is unsubstituted or substituted with halogen, oxo, hydroxy, lower alkyl, lower alkoxy, lower alkanoyloxy, lower cycloalkyl, lower cycloalkyloxy, aryl, aryloxy, heterocyclic group or heterocyclicoxy group; lower cycloalkyl; lower cycloalkyloxy; aryl, aryloxy, heterocyclic group or heterocyclicoxy group;

$R_3$ is hydrogen, lower alkyl, lower cycloalkyl, aryl or heterocyclic group, which comprises:

dispersing or mixing the bi-cyclic compound in a glyceride, and incorporating the liquid mixture in a soft-gelatin capsule whose shell comprises gelatin and a polyol selected from the group consisting of glycerin, propylene glycol and polyethylene glycol as a plasticizer.

6. The method of claim 5, wherein

A is —COOH or functional derivative thereof;

$X_1$ and $X_2$ are halogen;

$W_1$ is =O, or where one of $R_4$ and $R_5$ is hydrogen, another is hydroxy;

$W_2$ is where $R_4$ and $R_5$ are both hydrogen;

Z is oxygen;

$R_1$ is a saturated or unsaturated bivalent unsubstituted lower-medium aliphatic hydrocarbon residue;

$R_2$ is a saturated or unsaturated unsubstituted lower-medium aliphatic hydrocarbon residue;

$R_3$ is hydrogen.

7. The method of claim 5, wherein the polyol is glycerin.

8. The method of claim 7, wherein the glyceride is a medium chain fatty acid triglyceride.

9. The formulation of claim 1, wherein the mixture does not include polyethylene glycol as a vehicle.

10. The method of claim 5, wherein the mixture does not include polyethylene glycol as a vehicle.

* * * * *